United States Patent [19]

Takahashi et al.

[11] 4,205,051

[45] May 27, 1980

[54] STABILIZED ZIRCONIA FOR OXYGEN ION-CONDUCTIVE SOLID ELECTROLYTE

[75] Inventors: Takehiko Takahashi; Yutaka Suzuki, both of Nagoya, Japan

[73] Assignee: Toyota Jidosha Kogyo Kabushika Kaisha, Toyota, Japan

[21] Appl. No.: 933,478

[22] Filed: Aug. 14, 1978

[30] Foreign Application Priority Data

Oct. 15, 1977 [JP] Japan .................................. 52-123896

[51] Int. Cl.² ............................................. C01G 25/02
[52] U.S. Cl. ..................................... 423/266; 423/608; 106/57; 429/193
[58] Field of Search .................. 423/266, 608; 106/57; 429/193

[56] References Cited

U.S. PATENT DOCUMENTS

| | | | |
|---|---|---|---|
| 3,532,627 | 10/1970 | Mitoff et al. | 423/266 |
| 3,887,387 | 6/1975 | Sturhahn | 106/57 |
| 3,957,500 | 5/1976 | Pitts | 106/57 |
| 3,984,524 | 10/1976 | Alexandrov et al. | 423/608 |

FOREIGN PATENT DOCUMENTS

| | | | |
|---|---|---|---|
| 306106 | 7/1969 | U.S.S.R. | 106/57 |
| 381643 | 3/1971 | U.S.S.R. | 106/57 |

OTHER PUBLICATIONS

Spiridonov et al., "J. Solid State Chem.", vol. 2, 1970, pp. 430–438.

*Primary Examiner*—Herbert T. Carter
*Attorney, Agent, or Firm*—Brisebois & Kruger

[57] ABSTRACT

Stabilized zirconia for oxygen ion-conductive solid electrolyte, containing scandium oxide and ytterbium oxide having the following formula:

$$\alpha ZrO_2 \cdot \beta Sc_2O_3 \cdot \gamma Yb_2O_3$$

wherein $\alpha$, $\beta$, $\gamma$ are molar fractions; and $\alpha + \beta + \gamma = 1$.

3 Claims, 6 Drawing Figures

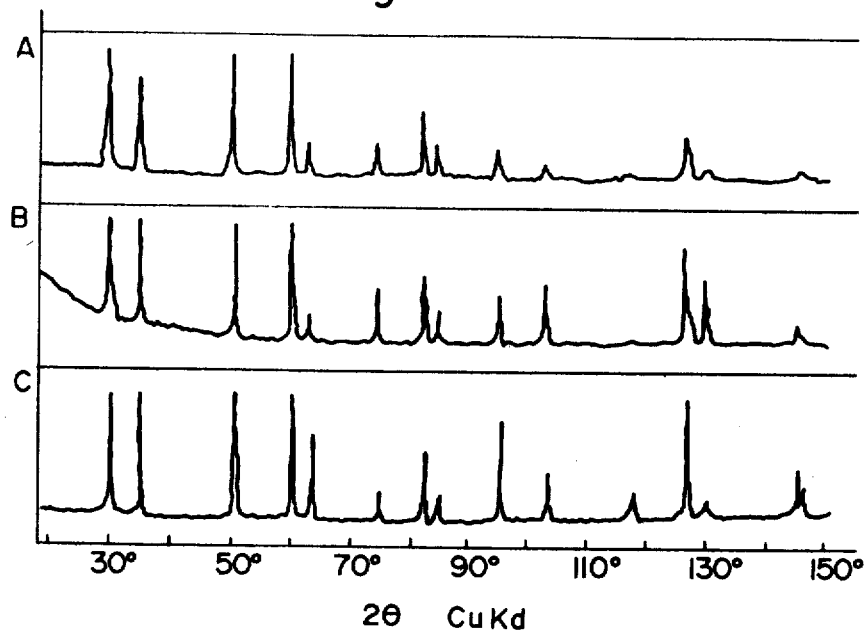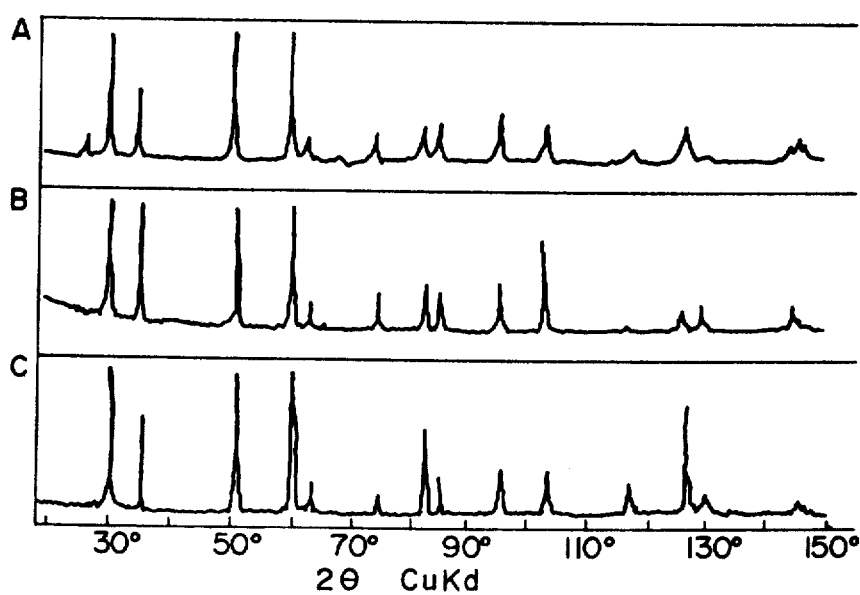

STABILIZED ZIRCONIA FOR OXYGEN ION-CONDUCTIVE SOLID ELECTROLYTE

BACKGROUND OF THE INVENTION

Stabilized zirconia doped with other metal ions is well-known as a good conductor of oxygen ions and it is widely being used as a solid electrolyte. It is prior art to add calcium oxide (CaO) or yttrium oxide ($Y_2O_3$) to zirconia for improving the phase stability and the oxygen ion conductivity of zirconia to be used as a high temperature type solid electrolyte [W. Nernst, Electrochmie, 6, 41 (1900)]. Such a stabilized zirconia, however, has the drawback that, when, for instance, it is applied in a fuel cell from which much current is to be drawn, its loading characteristic as a cell declines on account of its large impedance; and to eliminate this drawback, the working temperature has to be elevated.

Meanwhile, even when such a stabilized zirconia is to be used as a solid electrolyte for an auto lambda sensor, it is an important problem to lower the impedance of the solid electrolyte itself, because this sensor is desirable to work at around 300° C. Thus in the case of the conventional stabilized zirconia, its working temperature has to be elevated on account of the increased impedance.

It has also been known to use scandium oxide ($SC_2O_3$) as an additive for lowering the impedance of zirconia [F. M. Spiridonov et al., J. Solid State Chem. 2, 430 (1970)]; but in the case of a zirconia stabilized with only scandium oxide, since the ion radius of $Sc^{3+}$ is not so large as that of $Zr^{4+}$, the phase stability is not enough. Accordingly, this zirconia has the drawback that it is available only for use at high temperatures and therefore it cannot be suitably used as a general sensor.

BRIEF SUMMARY OF THE INVENTION

The object of this invention is to provide a stabilized zirconia characterized by low impedance and increased phase stability.

Another object of this invention is to provide a low-impedance and high-phase stability zirconia for use as a solid electrolyte.

BRIEF DESCRIPTION OF THE DRAWINGS

FIGS. 3 to 5 are X-ray diffraction patterns of the stabilized zirconia sintering in Example 1 when it is quenched from different temperatures.

DETAILED DESCRIPTION OF PREFERRED EMBODIMENTS

Figure 1:
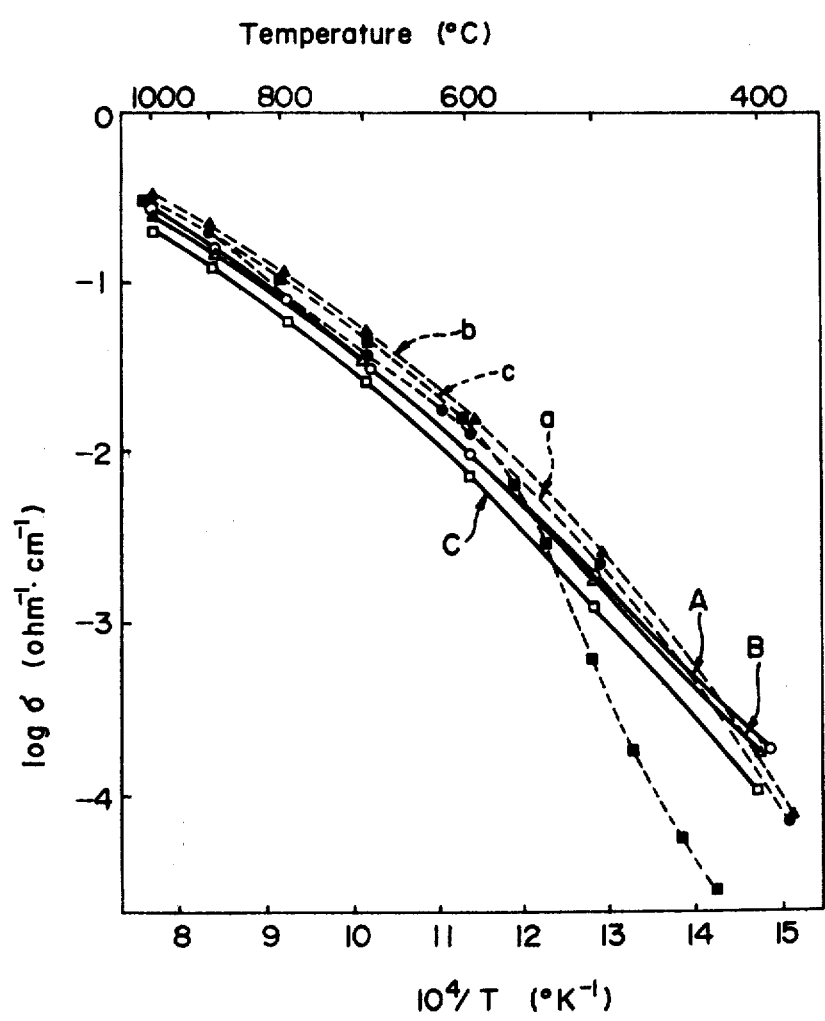
FIG. 1 is a diagram illustrating the conductivity change at different temperatures of stabilized zirconia sinterings obtainable from Example 1 and Reference example 1.

The stabilized zirconia of this invention has its phase stability enhanced through the addition of ytterbium oxide ($Yb_2O_3$) as a third element to the zirconium oxide ($ZrO_2$)-scandium oxide ($Sc_2O_3$) system and is characterized by being expressed by the following formula:

$$\alpha ZrO_2 \cdot \beta Sc_2O_3 \cdot \gamma Yb_2O_3$$

in which $\alpha$, $\beta$, $\gamma$ are molar fractions and $\alpha + \beta + \gamma = 1$.

To be specific, $\alpha$, $\beta$, $\gamma$ are in the following ranges:
$0.86 < \alpha < 0.94$
$0 < \beta < 0.14$
$0 < \gamma < 0.14$
; and desirably,
$0.88 < \alpha < 0.93$
$0 < \beta < 0.12$
$0 < \gamma < 0.12$ The above ranges of the molar fraction $\alpha$, $\beta$, $\gamma$ depend notably on the phase stability and oxygen ion conductivity of stabilized zirconia. The ratio between $\beta$ and $\gamma$, which differs in accordance with the intended use of a stabilized zirconia obtained therefrom, cannot be decided identically. For instance, when used as a solid electrolyte for a fuel cell from which a large current is to be drawn, it is desirable that the range is $\beta > \gamma$, thereby lowering the impedance. When it is used as a thermistor, the range is desirably $\beta < \gamma$, because the linearity of conductivity is vital and the phase stability at low temperatures has to be increased.

The stabilized zirconia may have a ratio between the molar fractions $\beta$ and $\gamma$ of from ⅓ to 3/1.

The stabilized zirconia of this invention will now be described in further detail. Usually the oxygen ion conductivity of a stabilized zirconia depends on the ion radius of the metal ion $M^{3+}$ or $M^{2+}$ that can be replaced with $ZR^{4+}$ ion. In this respect, the $Sc^{3+}$ ion whose ion radius is close to that of the $Zr^{4+}$ ion is found desirably for the purpose of increasing the oxygen ion conductivity; but on account of the $Sc^{3+}$ ion radius being too small to stabilize zirconia as a fluorite type cubic phase, the zirconia lacks phase stability at low temperatures.

Thus from among various compounds investigated, $Yb_2O_3$ has been selected as a third element to be added to zirconia, which fully meets the requirements that it does not reduce the ion conductivity of zirconia; it stabilizes zirconia as a cubic phase; and its electric charge is stable. As the particular reason for selecting $Yb_2O_3$, in the $ZrO_2-Yb_2O_3$ system this compound is stable as a solid solution at considerably low temperatures and the ion radius of $Yb^{3+}$ is the second closest to that of $Zr^{4+}$ after $Sc^{3+}$.

Stabilized zirconia of the $ZrO_2-SC_2O_3-Yb_2O_3$ system of the present invention keeps its relative effect even when sintered with a small addition of at least one compound like $Al_2O_3$ or $SiO_2$ as the sintering assistant.

As mentioned later in example 1, the stabilized zirconia of this invention can be obtained by a general method that a sintered product is formed through solid state reaction, solid solution reaction etc. of each raw material. That is to say, after measuring respectively predetermined quantities of $ZrO_2$, $Sc_2O_3$ and $Yb_2O_3$, they are fully mixed, for example, by an agate mortar and press-formed so that solid solution state reaction may be facilitated. Thereafter, the press-formed powder thus prepared is pre-sintered at 1,350° C. for 12 hours. Since the solid cannot be made sufficiently homogeneous by the above-mentioned treatment, the sintered product thus obtained is crushed again, and it is mixed, press-formed and sintered to give the product.

Besides the above-mentioned method, the method that solutions of Zr, Sc and Yb salts are mixed to give the raw material powder by coprecipitation and the sintered product is obtained from this powder can also be used.

The stabilized zirconia of the $ZrO_2$-$Sc_2O_3$-$Yb_2O_3$ system thus obtained, being nearly as well conductive as the conventional $ZrO_3$-$Sc_2O_3$ system, excelling in phase stability and retaining good conductivity even in the low temperature range below 600° C., can be used as a solid electrolyte to constitute the oxygen densitometer, the lambda sensor or the high-temperature type fuel cell or as a resistance for the thermistor.

The excellence of the stabilized zirconia of this invention in conductive characteristics and phase stability is further illustrated by the following examples. The present invention is not limited to these examples.

EXAMPLE 1

(1) Preparation of $ZrO_2$-$Sc_2O_3$-$Yb_2O_3$ System by Sintering

Commercially available $ZrO_2$, $Sc_2O_3$ and $Yb_2O_3$ (each of purity 99.9%) were blended in the proportions given in Table 1 so that the ratio of $\beta/\gamma = 1$ may be kept.

TABLE 1

| Samples | $ZrO_2$ $\alpha$ | $Sc_2O_3$ $\beta$ | $Yb_2O_3$ $\gamma$ |
|---|---|---|---|
| A | 0.92 | 0.040 | 0.040 |
| B | 0.91 | 0.045 | 0.045 |
| C | 0.90 | 0.050 | 0.050 |

($\alpha, \beta, \gamma$ are molar fractions of the general formula mentioned earlier; and $\alpha + \beta + \gamma = 1$.)

Respective mixtures were press-molded under 1 t/cm², where t is a metric ton, followed by 12 hours of calcining at 1,350° C. in the air. The sintering thus yielded was crushed again into powder and press-molded under 3 t/cm² into a disc. Then the disc was fired for 2 hours at 2,000° C. in the air.

The resulting final samples exhibited almost the same x-ray diffraction pattern as that of a solid solution of a fluorite type cubic phase, with apparent density 5.92 g/cm² for A, 5.88 g/cm² for B and 5.82 g/cm² for C.

(2) Measurement of Oxygen Ion Conductivity

Both surfaces of the samples A,B,C prepared in the above process were spattered with gold to form electrodes. Then the conductivites of these samples at each different temperature was determined by the a-c bridge method, the results being summarized in Table 2.

Table 2

| | (unit . ohm$^{-1}$ . cm$^{-1}$) Samples | | |
|---|---|---|---|
| °C. | A | B | C |
| 1,000 | $2.69 \times 10^{-1}$ | $2.44 \times 10^{-1}$ | $2.01 \times 10^{-1}$ |
| 800 | $8.25 \times 10^{-2}$ | $7.94 \times 10^{-2}$ | $6.07 \times 10^{-2}$ |
| 600 | $8.84 \times 10^{-3}$ | $8.84 \times 10^{-3}$ | $6.51 \times 10^{-3}$ |
| 400 | $1.78 \times 10^{-4}$ | $1.46 \times 10^{-4}$ | $8.45 \times 10^{-5}$ |

In FIG. 1, the relationships of Log $\sigma$-1/T are respectively represented by the solid lines A, B, C for the purposes of showing the conductivites obtained above. It is evident from FIG. 1 that the conductive characteristic, especially on the lineality of Arrhenius plot of the samples, of the samples A, B, C at temperatures lower than 600° C. has been improved.

(3) Measurement of Phase Stability

Figure 2:
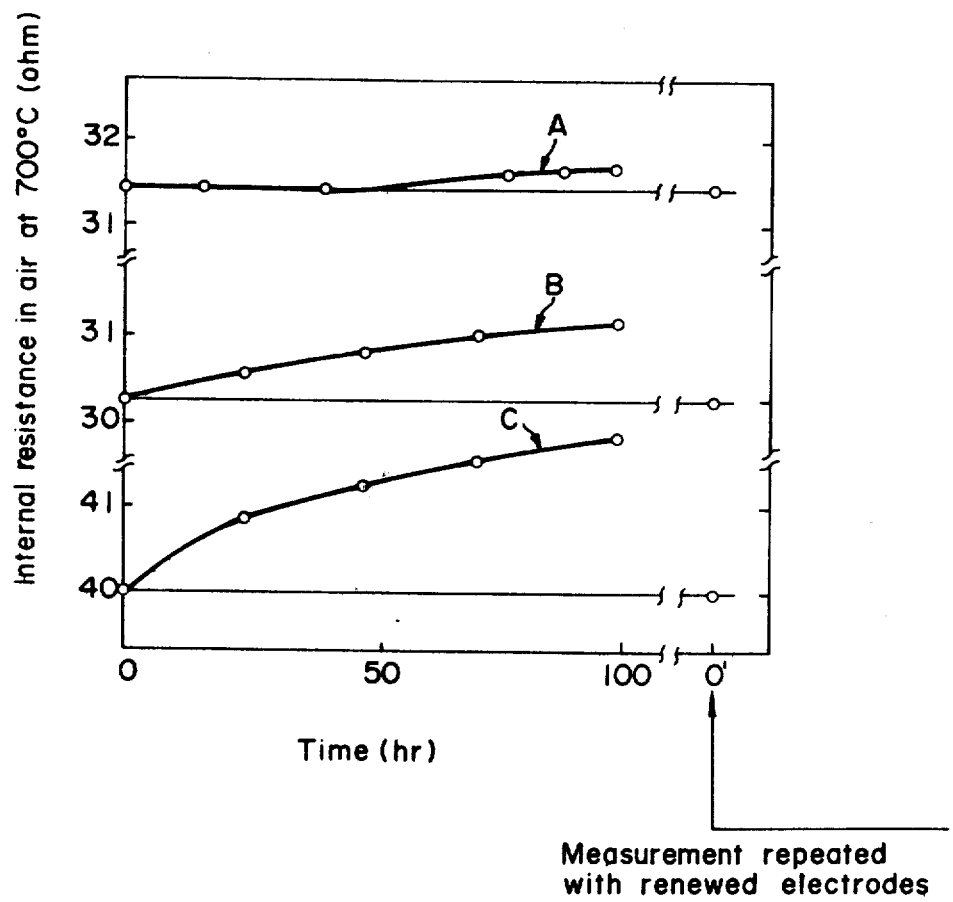
FIG. 2 is a diagram illustrating the aging changes of conductivity in the stabilized zirconia sintering in Example 1.

Aging change of conductivity in the samples A, B, C after 100 hours of heat treatment at 700° C. was measured, the results are summarized in FIG. 2. The aging change was due to deterioration of the electrode; in another measurement carried out with the electrode renewed it was revealed, as indicated at the right extreme (0') in FIG. 2, that the stabilized zirconia itself had not been aged at all.

Figure 5:
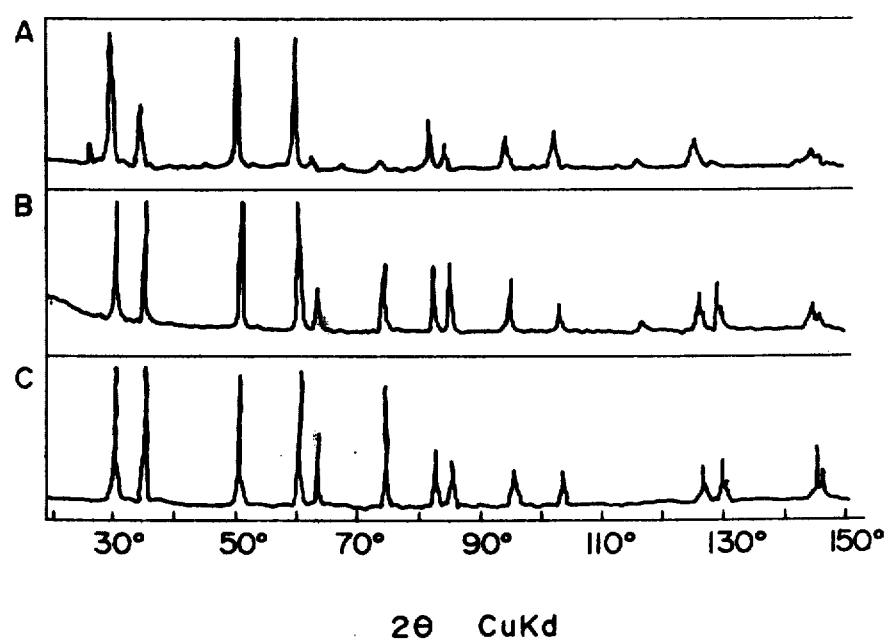

X-ray diffraction of each sample showed that in the sample A there is a very slight tetragonal system contained in the cubic system, but the samples B and C are purely cubic systems. Also when all the samples were subjected to 100 hours of heating at 1,000° C., 600° C. and 400° C., then quenched by dipping into water for rapid cooling, and thereafter X-ray diffracted, absolutely the same diffraction patterns were exhibited (FIGS. 3–5).

Thus the stabilized zirconia of the present invention may be called structurally very stable.

REFERENCE EXAMPLE 1

Using the same commercial materials and the same method as in Example 1, a two-component system sample composed of $ZrO_2$ and $Sc_2O_3$ was blended in the proportions listed in Table 3 and then fired.

TABLE 3

| Samples | $ZrO_2$ $\alpha$ | $Sc_2O_3$ $\beta$ | $Yb_2O_3$ $\gamma$ |
|---|---|---|---|
| a | 0.92 | 0.08 | 0 |
| b | 0.91 | 0.09 | 0 |
| c | 0.90 | 0.10 | 0 |

The oxygen ion conductivities of the samples a, b, c thus obtained were measured in the same manner as above, the results are represented by a broken line in FIG. 1.

It is evident from FIG. 1, a zirconia containing only $Sc_2O_3$ exhibits a slightly better conductivity in the high temperature range than the stabilized zirconia of the present invention, but with a heavy drop of conductivity in the low temperature range it lacks the system stability. cl REFERENCE EXAMPLE 2

Thermal stability tests were carried out on the above samples a, b, c as follows.

At the X-ray diffraction peak obtained when they were quenched with ice after an extremely long period of heating at over 800° C., these samples turned out to be practically a cubic phase with a slight content of tetragonal system. When 114 hours of heating at 400° C. was followed by quenching with ice, the samples a and b ($\beta = 0.08$–$0.09$) exhibited a diffraction peak of a cubic phase with a slight content of tetragonal system, but in the case of the sample c ($\beta = 0.1$) the diffraction pattern consisted mainly of a rhombic phase.

Thus it may be concluded that the $ZrO_2$-$Sc_2O_3$ system will be a stabilized as a cubic phase only when used in the high temperature range; and it will be very unstable in a cubic phase when used in the low temperature range.

EXAMPLE 2

Using the same commercial materials and the same process as in the preceding example 1, samples were prepared with the materials blended in proportions listed in Table 4 to give the ratio of $\beta/\gamma = 1/3$.

TABLE 4

| Samples | $ZrO_2$ $\alpha$ | $Sc_2O_3$ $\beta$ | $Yb_2O_3$ $\gamma$ |
| --- | --- | --- | --- |
| A' | 0.92 | 0.020 | 0.060 |
| B' | 0.91 | 0.023 | 0.067 |
| C' | 0.90 | 0.025 | 0.075 |

Figure 6:
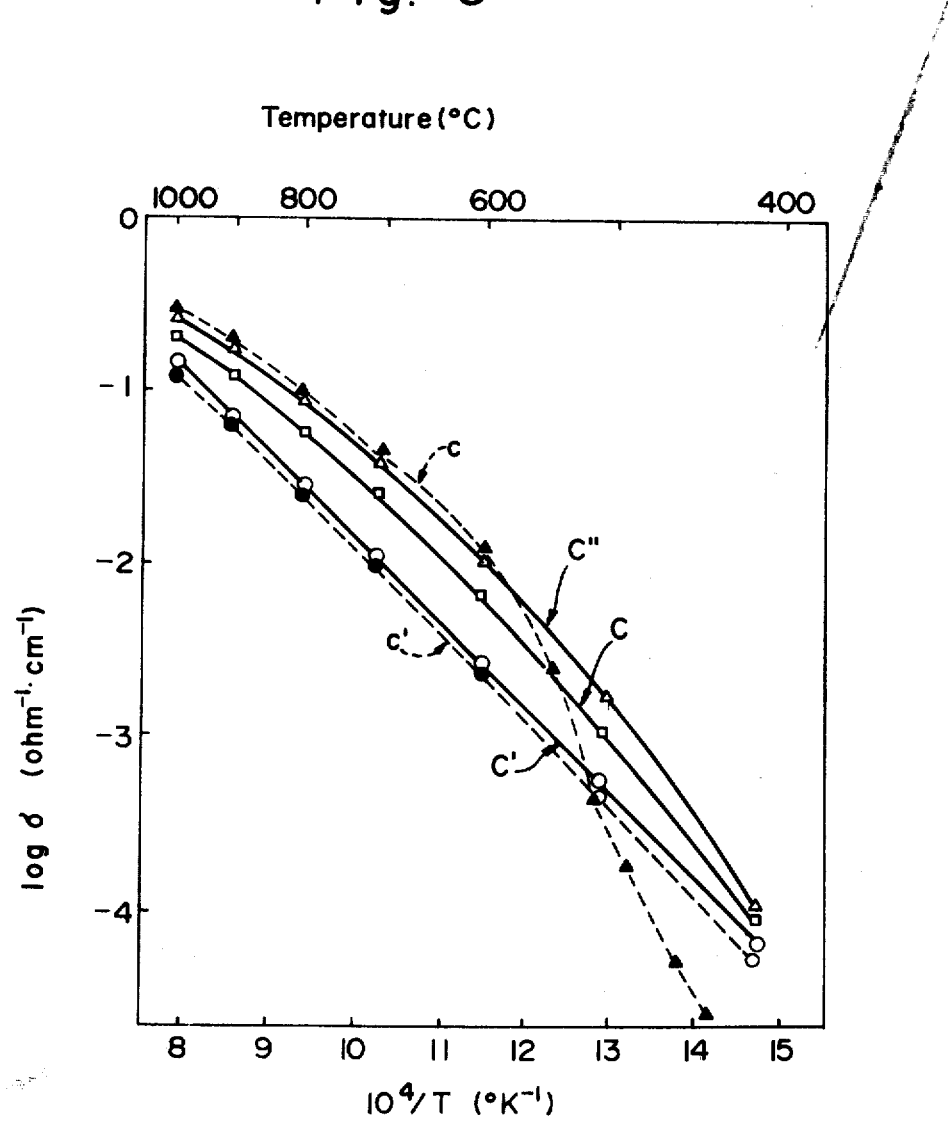
FIG. 6 is a diagram illustrating the conductivity changes at different temperatures in the stabilized zirconia sinterings obtainable from Examples 2, 3 and Reference example 3.

The conductive characteristic of the sample C' as illustrated in FIG. 6 is such that as compared with the sample C in Example 1, the conductivity is inferior in the order of 0.2–0.3, but the linearity in the low temperature range is rather superior to that of sample C.

Phase stability was checked similarly to Example 1–3 and it was found quite satisfactory.

EXAMPLE 3

Using the same materials as in Example 1 but blending them in proportions listed in Table 5 so as to give a ratio of $\beta/\gamma = 3/1$, samples were prepared by the same process as in Example 1.

TABLE 5

| Samples | $ZrO_2$ $\alpha$ | $Sc_2O_3$ $\beta$ | $Yb_2O_3$ $\gamma$ |
| --- | --- | --- | --- |
| A″ | 0.92 | 0.060 | 0.020 |
| B″ | 0.91 | 0.067 | 0.023 |
| C″ | 0.90 | 0.075 | 0.025 |

The conductive characteristic of the sample C″ as illustrated in FIG. 6 is such that in the high temperature range the conductivity is, though slightly, better than that of C in Example 1, while in the temperature range below 600° C., the drop in conductivity is rather heavy. The sample C″ with $\beta+\gamma=0.1$, however, is far more stable than the $0.9ZrO_2$-$0.1Yb_2O_3$ system using the same materials as mentioned in Reference example 3.

REFERENCE EXAMPLE 3

Using the same materials and the same process as above, a sample of $0.9ZrO_2$-$0.1Yb_2O_3$ system (with $\beta = 0$) was prepared and designated as C'. The conductive characteristic of C' as represented by a broken line in FIG. 6 is such that the linearity of correlation between $\log\sigma$ and $1/T$ is excellent but the conductivity is inferior to that of zirconia of the present invention. The conductivity of C in Reference example 1, also shown, suffers a heavy drop in the low temperature range.

What is claimed is:

1. Stabilized zirconia for an oxygen ion-conductive solid electrolyte, comprising zirconium oxide containing scandium oxide and ytterbium oxide having the formula:

$$\alpha ZrO_2 \cdot \beta Sc_2O_3 \cdot \gamma Yb_2O_3$$

wherein $\alpha$, $\beta$, $\gamma$ are molar fractions; and $\alpha+\beta+\gamma=1$, and the molar fractions $\alpha$, $\beta$, $\gamma$ are in the following ranges:

$0.86 < \alpha < 0.94$
$0 < \beta < 0.14$
$0 < \gamma < 0.14$.

2. The stabilized zirconia of claim 1, wherein the molar fractions $\alpha$, $\beta$, $\gamma$ are in the following ranges:

$0.88 < \alpha < 0.93$
$0 < \beta < 0.12$
$0 < \gamma < 0.12$.

3. The stabilized zirconia of claim 1, wherein the ratio between the molar fractions $\beta$ and $\gamma$ is from 1/3 to 3/1.

* * * * *